United States Patent
Savic et al.

(10) Patent No.: US 10,390,914 B2
(45) Date of Patent: Aug. 27, 2019

(54) METHOD FOR PROCESSING PREFABRICATED PROSTHETIC TEETH

(71) Applicant: Kulzer GmbH, Hanau (DE)

(72) Inventors: Novica Savic, Erlensee (DE); Karl-Heinz Renz, Alzenau (DE); Silke Maren Gall, Alzenau (DE)

(73) Assignee: Kulzer GmbH, Hanau (DE)

( * ) Notice: Subject to any disclaimer, the term of this patent is extended or adjusted under 35 U.S.C. 154(b) by 229 days.

(21) Appl. No.: 15/303,308

(22) PCT Filed: Apr. 9, 2015

(86) PCT No.: PCT/EP2015/057704
§ 371 (c)(1),
(2) Date: Oct. 11, 2016

(87) PCT Pub. No.: WO2015/155283
PCT Pub. Date: Oct. 15, 2015

(65) Prior Publication Data
US 2017/0035538 A1    Feb. 9, 2017

(30) Foreign Application Priority Data
Apr. 11, 2014   (DE) .................. 10 2014 105 190

(51) Int. Cl.
*A61C 13/12*    (2006.01)
*A61C 13/00*    (2006.01)
(Continued)

(52) U.S. Cl.
CPC .............. *A61C 13/12* (2013.01); *A61C 9/004* (2013.01); *A61C 13/0001* (2013.01);
(Continued)

(58) Field of Classification Search
CPC . A61C 13/12; A61C 13/1016; A61C 13/0001; A61C 9/004; A61C 13/08;
(Continued)

(56) References Cited

U.S. PATENT DOCUMENTS 1,518,075 A    12/1924   Kesling
9,295,534 B2    3/2016   Ruppert et al.
(Continued)

FOREIGN PATENT DOCUMENTS

DE    102005013459 A1    10/2006
DE    112007003610 T5     6/2010
(Continued)

OTHER PUBLICATIONS

International Preliminary Report on Patentability and Written Opinion in International Application No. PCT/EP2015/057704 dated Oct. 12, 2016, 17 pages.
(Continued)

*Primary Examiner* — William P Fletcher, III
(74) *Attorney, Agent, or Firm* — Marshall, Gerstein & Borun LLP

(57) ABSTRACT

A method for processing prosthetic teeth for the production of a full denture or at least a partial denture with at least two prosthetic teeth, a device for holding prosthetic teeth for the implementation of the method, and a set for the implementation of the method with the device. The method includes the following steps:
  inserting at least two prefabricated prosthetic teeth with their coronal sides into recesses of an elastic mold,
  attaching a clamping device to the elastic mold, and applying mechanical pressure to exert force to affix the prosthetic teeth in the elastic mold,
  positioning and aligning the prosthetic teeth in a desired position and a desired alignment in relation to each other in the elastic mold,
(Continued)

Figure 1:
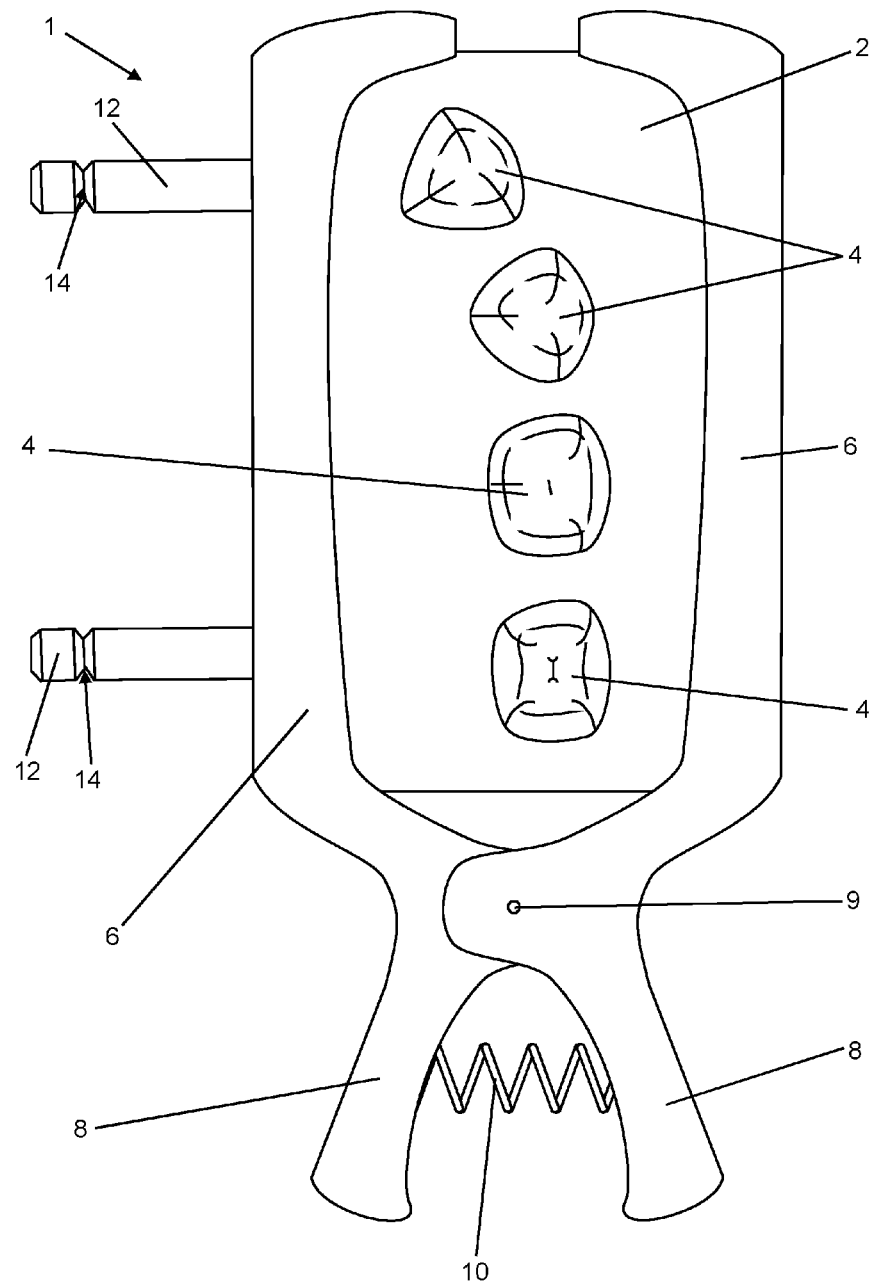

affixing the elastic mold with the clamping device and prosthetic teeth in a defined position in a holder of a CAM device for removing material of the prosthetic teeth with a CAM method, and basally ablating at least one of the prosthetic teeth affixed in the elastic mold with the CAM method.

25 Claims, 3 Drawing Sheets

(51) Int. Cl.
 A61C 13/08 (2006.01)
 A61C 13/10 (2006.01)
 A61C 9/00 (2006.01)
 A61C 13/107 (2006.01)
 A61C 13/36 (2006.01)
 G16H 20/40 (2018.01)

(52) U.S. Cl.
 CPC ...... *A61C 13/0004* (2013.01); *A61C 13/0006* (2013.01); *A61C 13/08* (2013.01); *A61C 13/1013* (2013.01); *A61C 13/1016* (2013.01); *G16H 20/40* (2018.01)

(58) Field of Classification Search
 CPC ............ A61C 13/0006; A61C 13/0004; A61C 13/1013; G16H 20/40
 See application file for complete search history.

(56) References Cited

U.S. PATENT DOCUMENTS

| 2006/0210945 | A1 | 9/2006 | Savic et al. |
| 2007/0190492 | A1* | 8/2007 | Schmitt ............ A61C 13/0004 433/213 |
| 2012/0276502 | A1 | 11/2012 | Marshall |
| 2014/0087327 | A1 | 3/2014 | Noack |
| 2014/0242549 | A1 | 8/2014 | Okada et al. |
| 2015/0216638 | A1* | 8/2015 | Baaske ................ A61C 13/00 433/196 |
| 2016/0193019 | A1 | 7/2016 | Heinz et al. |

FOREIGN PATENT DOCUMENTS

| DE | 102009056752 A1 | 6/2011 | |
| DE | 102011101678 A1 | 11/2012 | |
| EP | 2030590 A1 | 3/2009 | |
| EP | 2742907 A1 | 6/2014 | |
| JP | 2005-253756 A | 9/2005 | |
| WO | WO-2013/124452 A1 | 8/2013 | |
| WO | WO-2013124452 A1 * | 8/2013 | ........... A61C 9/0053 |

OTHER PUBLICATIONS

Search Report in International Application No. PCT/EP2015/057704 dated Jun. 18, 2015, 6 pages.

* cited by examiner

METHOD FOR PROCESSING PREFABRICATED PROSTHETIC TEETH

The invention relates to a method for processing prosthetic teeth for the production of a full denture or at least a partial denture with at least two prosthetic teeth.

The invention further relates to a device for holding prosthetic teeth for the implementation of such a method and a set for implementing such a method with such a device.

The invention thus relates to the production of prefabricated prosthetic teeth for further processing for partial plastic dentures (partial dentures) and full plastic dentures (full dentures), which are produced mechanically using a CAM method (CAM—Computer-Aided Manufacturing). Preferably, the dentures are constructed with the support of a computer using a CAD method (CAD—Computer-Aided Design). The prosthetic teeth can be provided as a semi-finished product for the partial or complete production of plastic dentures using a CAM method.

The current standard method is the analog creation of prosthetic teeth. Here, the prosthetic teeth are manually and individually set up on a wax base. In the next step, this wax prosthesis is embedded in dental plaster in a cuvette, and the wax base is washed out with hot water after the dental plaster has cured to create a hollow space for the denture resin. The prosthetic teeth remain in the dental plaster during this step. A respective dental plaster is injected or "plugged" into the hollow space to result in the denture or the finished prosthetic tooth after the plastic material has cured.

A set-up aid for processing tooth blocks is known form DE 10 2005 013 459 B4, in which the alignment of prosthetic teeth can be set to optimize the occlusion of the prosthetic teeth. During the setting up of prefabricated prosthetic teeth, said teeth are adjusted and ablated the dental technician to match the respective oral situation of the patient. First methods are already in existence, such as the methods known from DE 10 2009 056 752 A1 or WO 2013 124 452 A1, in which the partial or full denture is digitally set up and produced using CAD-CAM methods.

The disadvantage of this is that the correct positioning of the prosthetic teeth relative to each other in a denture base is difficult and errors can occur during this process. Usually, a form-fit mold is created in advance in a denture base in order to then glue in the prefabricated prosthetic teeth. However, this only works when sufficient space is available and the pf prosthetic teeth do not need to be ablated from below (basally). This tends to be the exception. In most cases, each prosthetic tooth must be ablated for space reasons. Prefabricated prosthetic teeth usually need to be at least basally processed within the scope of creating prosthetic works. When the process is manually implemented, it is conducted individually for each prosthetic tooth by the processor. In this case, however, it no longer fits into the pre-produced mold in the denture base.

DE 10 2011 101 678 A1 recommends embedding the crown area of a prosthetic tooth into a carrier layer in order to subsequently process the prosthetic tooth. This aims to achieve a firm, precise connection and at the same time a defined positioning of the prosthetic teeth. The disadvantage of this is that the prosthetic tooth must be exposed in some areas in order to process the crown area. The disadvantages of the method also lie in the costly production of the bodies. These must be produced individually or in groups by inserting the finished prosthetic teeth into a holder, setting on an outer frame and then pouring with a connection medium (e.g. wax). As a result, the pouring of the prosthetic teeth with the mass that forms the carrier layer requires a large amount of manual production time.

The carrier layer must be cured before the prosthetic tooth can be processed, since in particular when using automated CAM milling machines, considerable forces occur. The positioning precision of the method further suffers from possible deformations of the not yet fully cured carrier layer, so that in extreme cases, the post-processed prosthetic tooth cannot be sufficiently precisely milled and for this reason must be disposed of. Further, such a carrier layer can in most cases only be removed fully from the prosthetic tooth with a certain level of cost involved. The material for producing the carrier layer must be kept available and possibly mixed, melted or activated prior to application. After use, it must be disposed of. Further, when the individual processed prosthetic teeth are inserted, deviations may occur to the position and alignment of the prosthetic teeth in relation to each other.

The object of the invention is thus to overcome the disadvantages of the prior art. In particular, a method and a device should be provided with which as far as possible, a simple, complete and cost-efficient processing of the prosthetic teeth or production of the denture is enabled. Here, as few post-processing steps as possible should be necessary. As many necessary parts as possible should be re-usable. Post-processing of the finished post-processed prosthetic teeth should be avoided. Additionally, potential errors when inserting the prosthetic teeth into the denture base should be avoided. It should also be possible to implement the entire method in a simple manner and as far as possible mechanically and automatically.

The objects of the invention are attained by means of a method for processing prosthetic teeth for the production of a full denture or at least one partial denture with at least two prosthetic teeth, comprising the following method steps:

1) At least two prefabricated prosthetic teeth are inserted into an elastic mold, wherein the coronal sides of the prosthetic teeth are inserted into recesses in the elastic mold, 2) a clamping device is attached to the elastic mold or is already attached to the elastic mold, and after insertion of the prosthetic teeth into the elastic mold a mechanical pressure is applied to the elastic mold with the clamping device, wherein the pressure exerts a forces onto the prosthetic teeth inserted into the elastic mold via the elastic mold and thus the prosthetic teeth are affixed in the elastic mold, 3) the prosthetic teeth are positioned and aligned in the elastic mold in such a manner in relation to each other that at the latest following application of the clamping device on the elastic mold, the prosthetic teeth comprise the desired position and desired alignment in relation to each other which they should have in the partial denture to be produced or full denture to be produced, 4) the elastic mold is affixed with the clamping device and prosthetic teeth in a defined position in a holder of a CAM device for removing material of the prosthetic teeth with a CAM method, and 5) at least one of the prosthetic teeth affixed in the elastic mold is basally ablated with a CAM method.

A clamping device in the sense of the present invention is understood as being all devices with which a mechanical pressure can be applied to the elastic mold. Preferably, the force of at least two opposite directions is applied. Equally preferred, the directions of the force vectors which apply the pressure to the elastic mold are on one plane. The clamping device can in a preferred manner consist of a plastic material. Additionally, it can preferably be provided that the elasticity of the material of the clamping device is used to exert the mechanical pressure.

Preferably, all the prosthetic teeth affixed in the elastic mold are basally ablated using a CAM method.

Preferably, at least one basal side of at least one of the prosthetic teeth affixed in the elastic mold is processed in a computer-controlled manner using the CAM method, in particular processed with a CAM device.

Preferably, a plastic mold can be used as an elastic mold. In a particularly preferred manner, a solid silicon mold can be used. The silicon mold must be elastic in order to be able to insert the prosthetic teeth, but at the same time very hard so that during processing and the mechanical stresses on the prosthetic teeth which arise as a result, their position and alignment remains unchanged.

According to a particularly preferred embodiment of the present invention, the elastic mold comprises six recesses, so that six prosthetic teeth can be processed in the elastic mold. Preferably, all prosthetic teeth belong to one quadrant of the patient.

The elastic mold is structured as a single piece for the implementation of methods according to the invention. At least in the area of the recesses for holding the prosthetic teeth.

It is preferred according to the invention when several prosthetic teeth are affixed in two separate elastic forms respectively with two separate clamping devices. This has the advantage that then subsequently with a single work step, several prosthetic teeth held in the elastic forms can be processed in a single procedure and checked for their occlusion.

Further, it can be provided according to the invention that the prosthetic teeth which are affixed in the elastic mold, after at least one of the prosthetic teeth has been basally ablated, are connected on their basal side with a denture, wherein preferably, the prosthetic teeth are glued with their basal side in recesses provided for the purpose in the denture.

By this means, the production of the partial denture or partial dentures or the full denture is completed. The recesses of the denture base are preferably arranged as depressions in the denture base. In a particularly preferred manner, the side walls of the recesses fit with the outer surface of the prefabricated prosthetic teeth. The outer surface of the prosthetic teeth is the surface which is surrounded by the dental axis as a sheath, i.e. the surface which is arranged vertically to the coronal and basal end of the tooth or parallel to the dental axis. The outer surface is preferably the dental sheath surface. It is sufficient when the prefabricated prosthetic teeth comprise on the basal side an outer form or dental sheath surface which matches the side walls of the depression in the denture base. In a particularly preferred manner, the prefabricated prosthetic teeth comprise a cylindrical geometry on the basal side. The cylindrical geometry here also relates to general cylinders, i.e. not only cylinders with a circular base area.

Here, it can be provided according to the invention that following the connection of the prosthetic teeth with the denture base, the elastic mold is released from the prosthetic teeth, preferably after connecting the prosthetic teeth with the denture base, the clamping device is released or released from the elastic mold, and then subsequently, the elastic mold is released from the prosthetic teeth which are connected to the denture base.

By this means, it is achieved that the prosthetic teeth are inserted in the desired relative position and alignment to each other in the denture base.

With the invention, it is also recommended that the prosthetic teeth are positioned and aligned during insertion into the elastic mold in such a manner that the prosthetic teeth comprise the desired position and desired orientation in relation to each other which they should have in the partial denture or full denture to be produced.

As a result, the prosthetic teeth already attain the desired relative position and alignment in relation to each other during insertion into the elastic mold. This is advantageous in particular since the elastic mold should be as rigid as possible in order to avoid a change in the position and alignment of the prosthetic teeth in the elastic mold when material is being removed on the denture base.

It is further recommended that during basal ablation of at least one prosthetic tooth, the basal surface of the at least one prosthetic tooth which is generated by the ablation is calculated using a CAD method.

By this means, a further automation of the method for producing the denture or for positioning and processing the prosthetic teeth is achieved.

Further, it can here be provided that when calculating the basal surface to be created of the at least one prosthetic tooth, preferably all the prosthetic teeth affixed in the elastic mold, the surface of the denture base with which the prosthetic teeth are to be connected and the known position and alignment of the at least one prosthetic tooth relative to the other prosthetic tooth or the other prosthetic teeth is taken into account in the calculation.

With such a method, a further automation of the entire process can be achieved. In addition, the precision with which the denture is produced and thus the quality of the partial or full denture created is also improved.

Here it can in turn be provided according to the invention that the recess of the denture base with which the prosthetic teeth are to be connected is determined by a 3-dimensional scan of the oral cavity situation of a patient or a 3-dimensional scan of an imprint of the oral cavity situation of the patient, and by a computer-supported virtual set-up of the prosthetic teeth in the denture base.

With this method step also, a further automation of the entire process is improved.

With a further development of the invention, it is also recommended that the desired occlusion of the prosthetic teeth in relation to each other or the prosthetic teeth and the real teeth of the patient in relation to each other is determined in a computer-supported manner and is taken into account when calculating the basal surface of the CAD model of the at least one prosthetic tooth. Thus the occlusion should be taken into account when calculating the basal surface of the CAD model of the at least one prosthetic tooth to be processed, preferably naturally during the processing of all prosthetic teeth.

As a result, a post-processing of the partial or full denture produced can be avoided or at least reduced. Together with the joint set-up of the prosthetic teeth in the elastic mold or the elastic forms, when several devices are used to produce several partial dentures or for the production of a full denture, this can achieve a high degree of precision of the partial denture(s) or full denture produced.

Preferred designs of the method can also provide that the recesses in the elastic mold are sufficiently deep that they enclose the inserted prosthetic teeth at least in sections at a central circumference respectively.

By this means, a secure fixation of the position and alignment of the prosthetic teeth in relation to each other and to the CAM device is made possible. This is in particular important and advantageous during the basal processing of the prosthetic teeth.

Preferred methods can also provide that the inner surfaces of the recesses match, at least in certain areas, form-fit and flush-mounted to areas of the outer surfaces of the prosthetic teeth. Here, it can preferably be provided that the inner surfaces of the recesses correspond to negatives of the outer surfaces of the coronal sides of the prosthetic teeth.

By this means, a particularly stable affixation of the prosthetic teeth in the elastic mold can be achieved, in particular also with mechanical processing of the basal sides of the prosthetic teeth.

With a further development of the invention, it is recommended that the elastic mold is affixed with a retaining installation of the clamping device in the defined position in the holder of a CAM device for removing material of the prosthetic teeth with a CAM method, wherein the retaining installation is affixed in the holder, wherein preferably, the retaining installation is formed by two pins which are arranged on the outer side of the clamping device.

The retaining installation serves to provide the stable connection to the CAM device or a simple, uncomplicated ability to produce such a stable connection.

Further it is recommended that the elastic mold comprises an elasticity modulus of 10 MPa to 5,000 MPa, preferably an elasticity modulus of 50 MPa to 2,000 MPa, and in a particularly preferred manner, from 100 MPa to 1,000 MPa.

The elastic mold should be as rigid as possible in order to avoid a change to the position and support of the prosthetic teeth in the elastic mold during removal of material on the denture base. In particular when milling machines are used as CAM devices, the mill causes mechanical stress to be exerted on the prosthetic teeth, which should not lead, or not lead to an excessive degree, to the prosthetic teeth changing their position and alignment in relation to each other. This is advantageous since otherwise, the precision of the CAM method is reduced, since the precise alignment and position is a requirement for CAM methods. The elasticity moduli given are particularly well suited to this purpose.

Further, it can be provided according to the invention that the elastic mold consists of a material which rigidifies under pressure, or that the elastic mold is affixed following insertion of the prosthetic teeth, preferably through radiation or chemically.

As a result, a particularly stable affixation of the prosthetic teeth in the elastic mold is achieved, wherein at the same time, easy insertion of the prefabricated prosthetic teeth into the recesses of the elastic mold is made possible.

It is also recommended with the invention that a CAM-controlled milling installation for implementing the CAM method is used, preferably a CAM-controlled four-axle milling machine.

These CAM devices are particularly well suited to implementing the method.

Preferred methods according to the invention can provide that at least the outer forms of the basal sides of all prefabricated prosthetic teeth used are present as a first data set, and a second data set defines the precise positions and alignment of all prosthetic teeth affixed in the elastic mold, wherein a subsequent processing of the at least one prosthetic tooth is conducted on the basis of the first and second data set, preferably subsequent processing with a CAD/CAM method.

By this means, the advantages of the affixation according to the invention for fully automated post-processing methods, for which they are particularly well suited, are made accessible. It is namely only through the claimed affixation that a simple, cost-effective provision of the prosthetic teeth is made possible to a high degree of precision and position accuracy.

It is also recommended that the prefabricated prosthetic teeth used are produced prior to insertion into the elastic mold using a CAD method, wherein the data used to determine the outer form of the surface of the prefabricated prosthetic teeth is used to form the recesses in the elastic mold, wherein preferably, at least the recesses in the elastic mold are produced using a CAD/CAM method.

By this means, a further automation of the method according to the invention is achieved.

According to a further development of methods according to the invention, it can also be provided that prior to insertion of the prefabricated prosthetic teeth into the recesses of the elastic mold, an adhesion agent is applied in the surface of the recesses and/or onto the surfaces of the prosthetic teeth.

By this means, an even better retention of the prosthetic teeth in the recesses of the elastic mold can be achieved. The adhesive agent must however usually be removed again from the prosthetic teeth if it does not evaporate of its own accord.

According to a preferred embodiment of the method according to the invention, it can also be provided that in step 1), the prosthetic teeth are inserted into the recesses of the elastic mold in such a manner that the recesses fully enclose the prosthetic teeth on a central circumference respectively.

Due to this affixation on all sides of the prosthetic teeth, a particularly stable support, alignment and positioning of the prosthetic teeth relative to each other is possible.

The objects of the invention are also attained by means of a device for holding prosthetic teeth for implementing a method according to the invention, wherein the device comprises an elastic mold with at least two recesses for inserting prosthetic teeth and a clamping device which can be detachably affixed to the elastic mold for exerting a mechanical pressure onto the elastic mold, wherein the elastic mold comprises at least one retaining installation for connecting the constructed device to a CAM device for removing material of the prosthetic teeth inserted.

Here, it can be provided that the retaining installation comprises at least one latching means, which grips into a counter latching means of a CAM device, wherein preferably, the retaining installation comprises at least one pin with at least one circumferential groove as a latching means, which can be inserted into a holder opening of a CAM device.

With the latching means, a simple, secure connection of the device to the CAM device is possible.

Further alternative possible designs of the connecting means are click connections, tongue and groove or plug-in connections.

With the device, it can also be provided according to the invention that the elastic mold comprises an elasticity modulus of 10 MPa to 5,000 MPa, preferably an elasticity modulus of 50 MPa to 2,000 MPa, a particularly preferred an elasticity modulus of 100 MPa to 1,000 MPa.

By this means the advantages described above are provided.

With a further embodiment of the present invention, it is recommended that the prosthetic teeth can only be affixed in a specified position and alignment in the elastic mold.

It can also be provided that the elastic mold is a cylindrical elastic mold. Here, it can preferably be provided that the height of the cylindrical elastic mold lies between 2 mm and 15 mm. Additionally or as an alternative, it can be provided that the profile or diameter of the cylindrical elastic mold lies between 10 mm and 50 mm.

A cylindrical geometry is particularly well suited for the elastic form, since via the sheath surface, the pressure of the clamping device can in a particularly simple manner be evenly transferred onto the cylindrical elastic mold. The preferred dimensions are well suited for processing a prosthetic tooth or several prosthetic teeth.

The objects that form the basis of the invention are also attained by a set for implementing such a method comprising at least two prefabricated prosthetic teeth and at least one such device.

Finally, it can be provided that the set additionally contains a first data set relating to the outer form of all prefabricated prosthetic teeth and a second data set relating to the position of the affixed prefabricated prosthetic teeth in the recesses of the elastic mold, preferably on a data storage device.

By this means, a fully automated post-processing of the prosthetic teeth is facilitated.

The invention is based on the surprising finding that through the processing of prefabricated prosthetic teeth which are affixed in the desired position and alignment in relation to each other for the denture, it is possible to process the prosthetic teeth in such a manner that they fit with each other and as a result fit with the denture base, so that the denture produced very precisely contains the desired dimensions. At the same time, the occlusion of the denture with still existing teeth in the oral cavity of the patient, or the occlusion of two opposite dentures, can be taken into account and adjusted. With the present invention, falsely set up teeth and dentures which sit badly with regard to the occlusion can be avoided. The expense involved in fitting dentures produced according to the invention by the doctor is reduced. By affixing the hold of the prosthetic teeth in the recesses of the elastic mold, it becomes possible to insert the prosthetic teeth into the initially not yet tensioned elastic mold and at the same time to exploit the easier deformability of the elastic mold in order to insert the prosthetic teeth into well-fitting recesses. After the pressure is applied by the clamping device, the deformability of the elastic mold is reduced and the prosthetic teeth are held more strongly and thus more stably and with a more secure positioning and alignment for processing using the CAM method, so that the degree of precision during automated processing of the prosthetic teeth using the CAM method is high.

The method and the device and the set are particularly well suited for processing with CAD/CAM methods and are provided for the application of such techniques. The prosthetic teeth can be quickly and simply affixed. The clamping device can easily be re-used. Costly production of the holder, as is the case with wax holders, is no longer required with the method according to the invention. For some patients, the elastic mold can also be re-used without any problems arising, if for example a repair of the denture is required.

The clamping device and the entire device according to the invention are stable with regard to external influences such as heat or cold, and no distortion or deformations of the device or the clamping device occur, and thus no changes in position of the prosthetic teeth within the device or within the tensioned or pressed together elastic mold.

A further advantage of methods according to the invention lies in the very fast and almost tool- and auxiliary aid-free implementation. As a result, there is no necessity to have larger stock quantities available, and prefabrication is conducted on an order basis. The cleaning through boiling out or cleaning the prosthetic teeth, which is otherwise necessary when wax is used, is also no longer required.

The use of contact agents can further improve the connection between the elastic mold and the prosthetic teeth. As an exemplary contact agent, polyvinyl alcohol can be used, which after the evaporation of solvents contained forms an adhesive connecting layer.

The invention can for example provide that the prosthetic teeth are positioned by the user into the holder provided or elastic mold of the device provided such that during the CAM method they can be mechanically ground and thus adjusted to the individual situation of the base plate or the denture base and thus of the patient. Here, primarily the basal surface of the prosthetic teeth is ground, although after affixation of the prosthetic teeth in the denture base, the occlusal surface can also be mechanically processed for individual adjustment to the chewing function.

For this purpose, the prefabricated teeth are positioned and affixed in a pre-defined position within a holder tensioned into the machine. The holders (the devices according to the invention) are adjusted for this purpose to the application of such CAM methods, so that on the one hand they hold the individual prosthetic teeth sufficiently firmly, while on the other being sufficiently stable to be able to withstand successive milling processes without damage occurring.

The ready-made prefabricated prosthetic teeth are here held in a press fit by the pressure of the clamping device of the elastic mold.

The elastic mold preferably consists of largely deformation-stable material, for example an elastic plastic material such as silicon, polymethyl methacrylate (PMMA) or polyurethane (PU).

According to the invention, the elastic mold preferably has a thickness between 2 mm and 15 mm. Preferably, the elastic mold has the geometry of a general cylinder, which is pressed with the clamping device on its sheath surface.

The method according to the invention offers maximum flexibility during the digital production of partial and full dentures with regard to setting up the prosthetic teeth. With the method, classic prefabricated teeth or classic prefabricated prosthetic teeth can be used, which can be processed in the elastic mold with a CAM method by different machines. The ground prosthetic teeth can also be individually removed from the elastic mold.

Due to the fact that existing prefabricated prosthetic teeth can be used, prosthetic teeth can be used which are already tried and tested and recognised and popular on the market with regard to their function and aesthetic appearance. This means that should later repairs of a denture be required, classic prefabricated prosthetic teeth of the same type can be used on dental lamina. No block or blank needs to be mechanically ground or ablated, since the dental technician can also remove the prosthetic teeth from the dental lamina and insert them.

Figure 2:
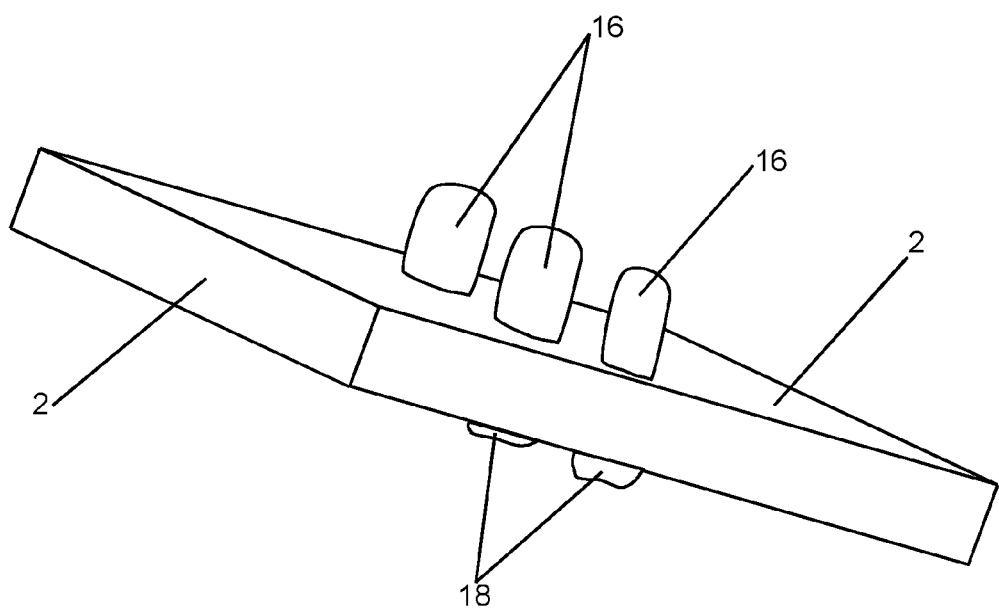
Figure 3:
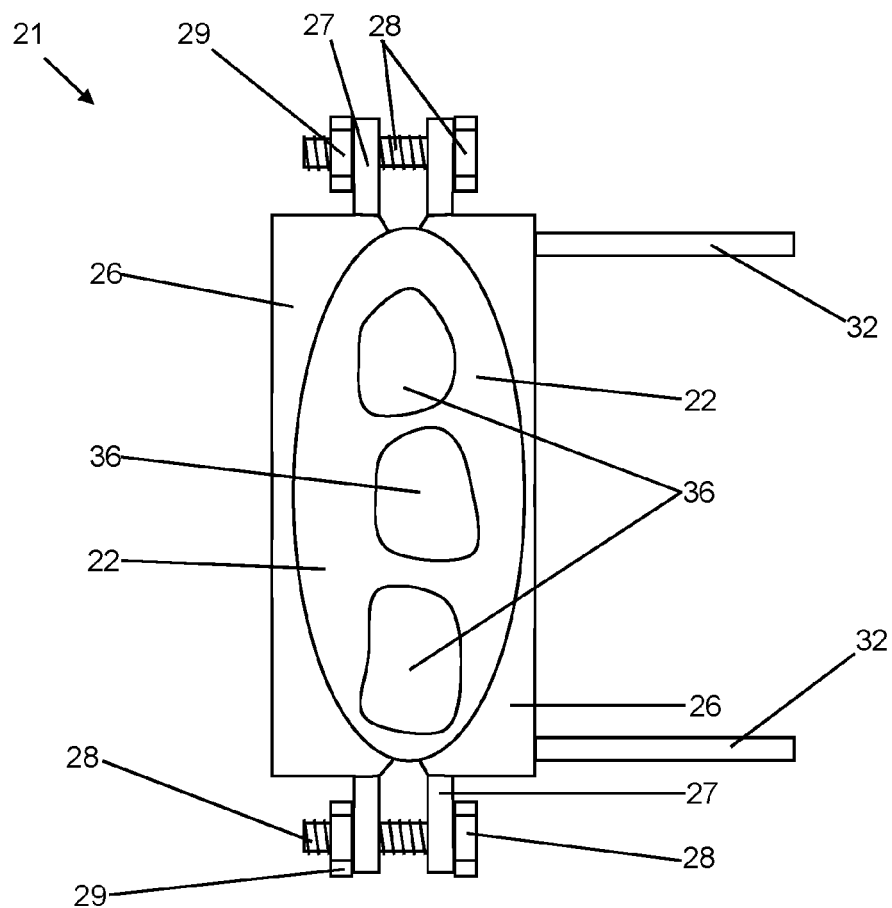

Exemplary embodiments of the invention are explained below with reference to three schematic figures, although without hereby restricting the invention, in which:

FIG. 1: shows a schematic top view onto a device according to the invention without inserted prosthetic teeth;

FIG. 2: shows a perspective view of an alternative elastic mold with inserted prosthetic teeth for the implementation of the method according to the invention;

FIG. 3: shows a schematic top view onto an alternative device according to the invention, in which three prosthetic teeth are affixed.

In the figures, the same reference numerals are used in part for similar parts in different embodiments.

FIG. 1 shows a schematic top view onto a device 1 according to the invention, in which no prosthetic teeth have been inserted. The prosthetic tooth holder 1 has an elastic mold 2 made of plastic, in which four recesses 4 are contained for holding the coronal sides of prefabricated prosthetic teeth (not shown). The recesses 4 are not continuous. The elastic mold 2 is structured, with the exception of the recesses, as a cylindrical block with a rounded base area. In the top view shown in FIG. 1, attention is drawn to one of the planar base areas of the cylindrical block.

The elastic mold 2 is enclosed in sections and for the most part by a clamping device 6 with two clamping arms. The two clamping arms open into a grip 8 so that the clamping device 6 can be operated in the manner of a clothes peg. The two parts of the clamping device 6 are pivoted around an axis 9 to form a connection with each other. An elastic steel spring 10 is arranged in the area of the grip 8. The steel spring 10 pushes the two parts of the grip 8 apart and thus the clamping arms together or towards each other. As a result, a pressure is exerted on the cylinder sheath of the elastic form 2, which due to the elasticity of the material continues through to the recesses 4. As a result, the prosthetic teeth (not shown) inserted into the recesses 4 can be affixed. The alignment and position of the inserted prosthetic teeth is determined by the position and alignment of the recesses 4 in the elastic mold 2. Through the force which is exerted by the clamping device 6 onto the elastic mold 2, the elastic mold 2 can deform and thus differentiate between the position and alignment of the affixed prosthetic teeth and that of the non-affixed prosthetic teeth.

On one side of the clamping device 6, two pins 12 are affixed as a retaining installation, with which the entire device 1 can be tensioned into a CAM milling machine (not shown) or affixed in a CAM milling machine. On the pins 12, circumferential grooves 14 are provided as latching means 14, which grip into a counter-latching means (not shown) of the CAM milling machine, and in so doing affix the entire device 1 in the CAM milling machine in a firm location and stable position.

The prefabricated prosthetic teeth are inserted with their coronal sides or coronal ends at the front into the recesses 4 of the elastic mold 2. Due to the characteristic form of the prosthetic teeth, these can only be inserted in one alignment and position. During insertion, the recesses 4 can deform even more easily, so that a firm seat of the prosthetic teeth in the recesses 4 can be achieved due to the fact that when the recesses 4 deform back, the surface of the recesses 4 lies in a form-fit manner in contact with the coronal sides of the prosthetic teeth which are fully inserted into the recesses 4. The clamping device 6 is then applied and a pressure is exerted onto the elastic mold 2, and by this means the prosthetic teeth are affixed in the elastic mold 2.

The entire device 1 is tensioned into the fully automated CAM 4-axle milling machine with the aid of the pins 12. The basal sides of the prosthetic teeth which protrude from the recesses 4 are then ground, so that their basal form corresponds to the surface of recesses of a denture base into which the prosthetic teeth are to be inserted.

Due to the known dimensions and fixed-location and fixed-position affixation of the device 1 and thus of the prefabricated prosthetic teeth affixed in it, it is possible for the CAM milling machine to basally mill off the prosthetic teeth protruding from the recesses 4 and thus from the device 1 based on a virtual computer model (preferably a calculated CAM mode) and to adjust them to recesses for said prosthetic teeth in the denture base, the outer form of which is also known and which is taken into account in the calculation of the basal surface of the prosthetic teeth to be achieved through milling off.

After the prosthetic teeth have been ablated to the desired form, they can still be affixed in the device 1 in a holder or also individual in the denture base, wherein the prosthetic teeth are glued into the denture base. The correct position and arrangement (or position and alignment) is already guaranteed by the device 1. Then the clamping device 6 is removed and the elastic mold 2 is removed from the prosthetic teeth.

In order to attain the desired position and alignment of the prosthetic teeth in the elastic mold 2, the elastic mold is preferably created using a fully automated CAD-CAM method, based on the same data also used to produce and process the denture base and prosthetic teeth.

FIG. 2 shows a perspective view of an alternative elastic mold 2 with inserted prosthetic teeth 16, 18 for implementing a method according to the invention. The elastic mold 2 shown in FIG. 2 differs from that in FIG. 1 by the fact that the recesses in the elastic mold 2 are continuous, so that when the prosthetic teeth 16, 18 are inserted, both the basal sides 16 and the coronal sides 18 are visible. Since as a result the bearing of the prosthetic teeth 16, 18 is impaired, for such an elastic mold, a more rigid plastic or a plastic with a higher elasticity modulus is preferred. Additionally, in this elastic mold 2, only three prosthetic teeth 16, 18 are inserted. The elastic mold shown in FIG. 2 thus only has three recesses in which the prosthetic teeth 16, 18 are inserted.

Thus it is possible to process both the coronal sides 18 and the basal sides 16 of the prosthetic teeth 16, 18. The prosthetic teeth 16, 18 are according to the embodiment shown in FIG. 2 therefore inserted through the recesses of the elastic mold 2. The affixation of the prosthetic teeth 16, 18, like the subsequent processing, is conducted as shown in FIG. 1, except for the fact that both sides 16, 18 can be processed.

FIG. 3 shows a schematic top view onto an alternative device 21 according to the invention, in which three prosthetic teeth 36 are affixed.

In the device 21 shown, three prosthetic teeth 36 are affixed in three recesses (not visible, since they are covered by the prosthetic teeth 36) of an elastic mold 22. The elastic mold 22 consists of a plastic material and has a cylindrical form with oval base areas. By means of the top view, the basal areas of the prosthetic teeth 36, i.e. the basal sides 36 of the prosthetic teeth 36, can be seen in FIG. 3. The elastic mold 22 is pressed together by two clamping brackets 26 of a clamping device 26. In contrast to the embodiment shown in FIG. 1, the pressure is not exerted onto the elastic mold by an elastic compression spring by with the aid of a bolt system.

On two opposite sides of the clamping brackets 26, a perforated plate 27 is affixed respectively, via which the clamping brackets 26 can be affixed to each other. The affixation is conducted with one bolt 28 each, which is respectively inserted through holes in the perforated plates 27 of both clamping brackets 26, and which is affixed on the opposite side by one counter nut 29 respectively.

The prosthetic teeth 36 lie in contact in a form-fit and flush-mounted manner in three recesses each of the elastic mold 22. Due to the distance of the two clamping brackets 26, the entire pressure is applied to the elastic mold 22, which transfers the pressure onto the prosthetic teeth 36, so that a particularly stable hold is achieved. The pressure here comes from two directions in particular (in FIG. 3 from the right and left), while the holding force in the vertical direction to it (from top to bottom in FIG. 3) is weaker than with a fully encompassing fitting form. By setting the torque with which the bolts 28 are tightened against the counter nuts 29, a defined force can be exerted onto the elastic mold 22 and thus onto the prosthetic teeth 36.

If a particularly stable affixation on all sides with an even more uniform force application onto the prosthetic teeth 36 is to be achieved from all directions, a clamp ring in the style of a hose clamp ring can be used for affixation purposes. The clamp encloses the elastic mold 22 for this purpose.

On the clamping device 26, two pins 32 are arranged with which the device 21 can be affixed in a CAM device.

It is particularly advantageous for the present invention when a surface or form-fit pressure is to be applied to the prosthetic teeth 16, 18, 36 and the elastic mold 2, 22.

The features of the invention disclosed in the above description and in the claims, figures and exemplary embodiments can be essential both individually and in any desired combination for the realization of the invention in its different embodiments. Naturally, the method and the device for the indicated numbers of prosthetic teeth 16, 18, 36, together with the exemplary embodiments shown with three or four prosthetic teeth 16, 18, 36, can be transferred in a simple manner to other numbers of prosthetic teeth 16, 18, 36. Preferably, several of the prosthetic tooth holders 1, 21 shown or devices 1, 21 according to the invention for implementing a method according to the invention can also be used. It is then possible to check and adjust the occlusion of prosthetic teeth 16, 18, 36 arranged opposite each other inserted into the oral cavity of the patient.

LIST OF REFERENCE NUMERALS 1, 21 Prosthetic tooth holder
2, 22 Elastic mold
4 Recess with coronal tooth form
6, 26 Clamping device/jaw
8 Grip
9 Axis
Spring
12,32 Pin/holder
14 Groove/latching means
16, 36 Prosthetic tooth basal side
18 Prosthetic tooth coronal side
26 Clamping bracket
27 Perforated plate
28 Bolt
29 Nut

The invention claimed is:

1. A method for processing prosthetic teeth for the production of a full denture or at least a partial denture with at least two prosthetic teeth comprising the following method steps:
   (a) inserting at least two prefabricated prosthetic teeth having coronal sides and basal sides into an elastic mold, wherein the coronal sides of the prosthetic teeth are inserted into recesses in the elastic mold,
   (b) attaching a clamping device to the elastic mold if a clamping device is not already attached to the elastic mold, and after inserting the prosthetic teeth into the elastic mold, applying a mechanical pressure to the elastic mold with the clamping device, wherein the pressure exerts a force onto the prosthetic teeth inserted into the elastic mold via the elastic mold and the prosthetic teeth are thereby affixed in the elastic mold,
   (c) positioning and aligning the prosthetic teeth in the elastic mold in such a manner in relation to each other that the prosthetic teeth comprise a desired position and desired alignment in relation to each other which they should have in the partial denture to be produced or full denture to be produced,
   (d) affixing the elastic mold with the clamping device and prosthetic teeth in a defined position in a holder of a CAM device for removing material of the prosthetic teeth with a CAM method,
   (e) basally ablating at least one of the prosthetic teeth affixed in the elastic mold with the CAM method,
   (f) connecting the prosthetic teeth affixed in the elastic mold to a denture base on their respective basal sides after at least one of the prosthetic teeth has been basally ablated, and
   (g) following connecting the prosthetic teeth to the denture base, releasing the elastic mold from the prosthetic teeth.

2. The method according to claim 1, comprising positioning and aligning the prosthetic teeth during insertion into the elastic mold in such a manner that the prosthetic teeth comprise the desired position and a desired orientation in relation to each other which they should have in the partial denture or full denture to be produced.

3. The method according to claim 1, comprising during the basal ablation of the at least one of the prosthetic teeth, calculating a basal surface of the at least one of the prosthetic teeth which is generated by the ablation with the CAD method.

4. The method according to claim 3, comprising calculating a basal surface to be created on the at least one of the prosthetic teeth affixed in the elastic mold as a function of the surface of the denture base with which the prosthetic teeth are to be connected and the known position and alignment of the at least one of the prosthetic teeth relative to another prosthetic tooth or other prosthetic teeth in the calculation.

5. The method according to claim 4, comprising determining a recess of the denture base with which the prosthetic teeth are to be connected by a 3-dimensional scan of an oral cavity situation of a patient or a 3-dimensional scan of an imprint of the oral cavity situation of the patient, and by a computer-supported virtual set-up of the prosthetic teeth in the denture base.

6. The method according to claim 4, comprising calculating the basal surface to be created on all the prosthetic teeth affixed in the elastic mold as a function of the surface of the denture base with which the prosthetic teeth are to be connected and the known position and alignment of each of the prosthetic teeth relative to the other prosthetic teeth in the calculation.

7. The method according to claim 3, comprising determining a desired occlusion of the prosthetic teeth in relation to each other or the prosthetic teeth and the real teeth of the patient in relation to each other in a computer-supported manner and calculating a basal surface of a CAD model of the at least one prosthetic tooth based on said determined desired occlusion.

8. The method according to claim 1, wherein the recesses in the elastic mold are sufficiently deep that they enclose the inserted prosthetic teeth at least in sections of the elastic mold at a central circumference of the inserted prosthetic teeth respectively.

9. The method according to claim 1, wherein inner surfaces of the recesses at least in sections match in a form-fit and are flush-mounted to areas of the outer surfaces of the prosthetic teeth.

10. The method according to claim 9, wherein the inner surfaces of the recesses correspond to negatives of outer surfaces of the coronal sides of the prosthetic teeth.

11. The method according to claim 1, wherein the elastic mold is affixed with a retaining installation of the clamping device in the defined position in the holder of a CAM device for removing material of the prosthetic teeth with a CAM method, and wherein the retaining installation is affixed in the holder.

12. The method according to claim 11, wherein the retaining installation is formed by two pins which are arranged on an outer side of the clamping device.

13. The method according to claim 1, wherein the elastic mold comprises an elasticity modulus of 10 MPa to 5,000 MPa.

14. The method according to claim 13, wherein the elastic mold comprises an elasticity modulus of 50 MPa to 2,000 MPa.

15. The method according to claim 13, wherein the elastic mold comprises an elasticity modulus of 100 MPa to 1,000 MPa.

16. The method according to claim 1, wherein the elastic mold comprises a material which rigidifies under pressure, or that the elastic mold is affixed following insertion of the prosthetic teeth.

17. The method according to claim 16, wherein the elastic mold is affixed with the clamping device through radiation or chemically.

18. The method according to claim 1, wherein at least outer forms of the basal sides of all prefabricated prosthetic teeth used are present as a first data set, and a second data set defines precise positions and alignment of all prosthetic teeth affixed in the elastic mold, the method comprising conducting a subsequent processing of the at least one prosthetic tooth as a function of the first data set and the second data set.

19. The method according to claim 18, wherein the subsequent processing is conducted with a CAD/CAM method.

20. The method according to claim 1, comprising producing the prefabricated prosthetic teeth prior to insertion into the elastic mold with a CAD method, and determining the outer form of the surface of the prefabricated prosthetic teeth to form the recesses in the elastic mold.

21. The method according to claim 20, comprising producing at least the recesses in the elastic mold with a CAD/CAM method.

22. The method according to claim 1, comprising prior to insertion of the prefabricated prosthetic teeth into the recesses of the elastic mold, applying an adhesion agent in the surface of the recesses and/or onto the surfaces of the prosthetic teeth.

23. The method according to claim 1, comprising in step (a), inserting the prosthetic teeth into the recesses of the elastic mold in such a manner that the recesses fully enclose the prosthetic teeth on a central circumference of the inserted prosthetic teeth.

24. The method according to claim 1, wherein the prosthetic teeth are glued with their respective basal sides in recesses in the denture base provided for the purpose.

25. The method according to claim 1, further comprising after releasing the clamping device from the elastic mold, releasing the elastic mold from the prosthetic teeth which are connected to the denture base.

* * * * *